United States Patent
Chishti et al.

(10) Patent No.: US 6,685,469 B2
(45) Date of Patent: *Feb. 3, 2004

(54) SYSTEM FOR DETERMINING FINAL POSITION OF TEETH

(75) Inventors: Muhammad Chishti, Sunnyvale, CA (US); Andrew Beers, Redwood City, CA (US)

(73) Assignee: Align Technology, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/047,078

(22) Filed: Jan. 14, 2002

(65) Prior Publication Data

US 2002/0064748 A1 May 30, 2002

Related U.S. Application Data

(63) Continuation of application No. 09/313,291, filed on May 13, 1999, now Pat. No. 6,406,292.

(51) Int. Cl.[7] .................................. A61C 3/00
(52) U.S. Cl. ....................................... 433/24
(58) Field of Search ................... 433/6, 24, 213

(56) References Cited

U.S. PATENT DOCUMENTS

| | | |
|---|---|---|
| 3,660,900 A | 5/1972 | Andrews |
| 3,860,803 A | 1/1975 | Levine |
| 4,504,225 A | 3/1985 | Yoshii |
| 4,505,673 A | 3/1985 | Yoshii |
| 4,755,139 A | 7/1988 | Abbatte et al. |
| 4,793,803 A | 12/1988 | Martz |
| 4,798,534 A | 1/1989 | Breads |
| 4,836,778 A | 6/1989 | Baumrind et al. |
| 4,856,991 A | 8/1989 | Breads et al. |
| 4,936,862 A | 6/1990 | Walker et al. |
| 5,011,405 A | 4/1991 | Lemchen |
| 5,017,133 A | 5/1991 | Miura |
| 5,035,613 A | 7/1991 | Breads et al. |
| 5,055,039 A | 10/1991 | Abbatte et al. |
| 5,059,118 A | 10/1991 | Breads et al. |
| 5,139,419 A | 8/1992 | Andreiko et al. |
| 5,186,623 A | 2/1993 | Breads et al. |
| 5,273,429 A | 12/1993 | Rekow |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,382,164 A | 1/1995 | Stern |
| 5,395,238 A | 3/1995 | Andreiko et al. |

(List continued on next page.)

FOREIGN PATENT DOCUMENTS

| | | |
|---|---|---|
| FR | 2 369 828 | 6/1978 |
| WO | WO 94/10935 | 5/1994 |
| WO | WO98/32394 A1 | 7/1998 |

OTHER PUBLICATIONS

Laurendeau et al., "A Computer–Vision Technique for the Acquisition and Processing of 3-D Profiles of Dental Imprints: An Application in Orthodontics" *IEEE Transactions on Medical Imaging* (Sep. 1991) 10(3):453–461.

Doyle, "Digital Dentistry" *Computer Graphics World* (Oct. 2000) pp. 50–52, 54.

Redmond et al., "Clinical Implications of Digital Orthodontics" *Am. J. Orthodont. Dentofacial Orthopedics* (2000) 117(2):240–242.

(List continued on next page.)

*Primary Examiner*—John J. Wilson
(74) *Attorney, Agent, or Firm*—Townsend and Townsend and Crew LLP; Bao Tran, Esq.

(57) ABSTRACT

An apparatus and method define a fit a set of upper and lower teeth in a masticatory system of a patient by generating a computer representation of the masticatory system of the patient; and determining an occlusion from the computer representation of the masticatory system using one or more keys.

58 Claims, 7 Drawing Sheets

U.S. PATENT DOCUMENTS

| | | | |
|---|---|---|---|
| 5,431,562 A | 7/1995 | Andreiko et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| 5,533,895 A | 7/1996 | Andreiko et al. |
| 5,542,842 A | 8/1996 | Andreiko et al. |
| 5,549,476 A | 8/1996 | Stern |
| 5,587,912 A | 12/1996 | Andersson et al. |
| 5,605,459 A | 2/1997 | Kuroda et al. |
| 5,607,305 A | 3/1997 | Andersson et al. |
| 5,645,421 A | 7/1997 | Slootsky |
| 5,683,243 A | 11/1997 | Andreiko et al. |
| 6,217,334 B1 | 4/2001 | Hultgren |

OTHER PUBLICATIONS

"DentSim . . . Dent–X's virtual reality 3–D training simulator . . . A revolution in dental education," downloaded from www.dent–x.com/DentSim.htm, Sep. 24, 1998, 6 pgs.

Biostar Operation & Training Manual, Great Lakes Orthodontics, Ltd. 199 Fire Tower Drive, Tonawanda, New York, 14150–5890, 20 pgs.

Chiappone, "constructing the gnathologic setup and positioner," J. Clin. Orthod., 1980, 14:121–133.

Cottingham, "Gnathologic clear plastic positioner," Am. J. Orthod. 1969, 55:23–31.

Cureton, "Correcting malaligned mandibular incisors with removable retainers," J. Clin. Orthod. 1996. 30:390–395.

Elsasser, "Some observations on the history and uses of the Kesling positioner," Am. J. Orthod. 1950, 36:368–374.

Kamada et al., "Case reports on tooth positioners with LTV vinyl silicone rubber and some case reports," J. Nihon University School of Dentistry 1982, 24(1):1–27.

Kamada et al., "Construction of Tooth Positioners with LTV Vinyl Silicone Rubber and Some Case Reports," J. Nihon University School of Dentistry Mar. 1982, 24(1):1–26.

Kesling, "Coordinating the predetermined pattern and tooth positioner with conventional treatment," Am. J. Orthod. Oral. Surg. 1946, 32:285–293.

Kesling, "The philosophy of the tooth positioning appliance," Am. J. Orthod. Oral. Surg. 1945, 31(6):297–304.

Kleeman et al., "The speed positioner," J. Clin. Orthod. 1996, 30:673–680.

Kunii et al., "Abstract: Articulation simulation for an intelligent dental care system," Displays, vol. 15, No. 1, 1994, 9 pgs.

Kuroda et al., "Three–dimensional dental cast analyzing system using laser scanning," Am. J. Orthod. Dentofac. Orthop. 1996, 110:365–369.

Lawrence F. Andrews, D.D.S., "Straight Wire, The Concept and Appliance," The Six Keys to Optimal Occlusion, 15–24.

Lawrence F. Andrews, D.D.S., "The six to normal occlusion," Am. J. Orthod. Sep. 1972, 296–308.

Nippon Dental Review, "New orthodontic device–dynamic positioner (D.P.)—I Approach to the proposal of D.P. and transparent silicone rubber," 1980, 452:61–74.

Nippon Dental Review, "New orthodontic device–dynamic positioner (D.P.)—II, Practice application and construction of D.P. and transparent silicone rubber," 1980, 454:107–130.

Nippon Dental Review, "New orthodontic device–dynamic positioner (D.P.)—III, Case reports of reversed occlusion," 457:146–164.

Nippon Dental Review, "New orthodontic device–dynamic positioner (D.P.)—Case reports of reversed occlusion," 1980, 458:112–129.

Nishiyama et al., "A new construction of tooth repositioner by LTV vinyl silicone rubber," J. Nihon Univ. School of Dentistry 1977, 19(2):93–102.

Raintree Essix & ARS Materials, Inc., Raintree Essix, Technical Magazine Table of contents and Essix Appliances, httpz;//www.essix.com/magazine/default.html Aug. 13, 1997, 7 pgs.

Richmond et al., "The development of the PAR Index (Peer Assessment Rating): reliability and validity," EU Journal of Orthodontics 14, 1992, 15 pgs.

Schroeder et al., "Algorithms 1," The Visualization Toolkit chapter 6–9.9, 1996.

Shilliday, "Minimizing finishing problems with the mini–positioner," Am. J. Orthod. 1971, 59:596–599.

Warunek et al., "Clinical Use of Silicone Elastomer Appliances," JCO Oct. 1989, 694–700.

Warunek et al., "Physical and mechanical properties of elastomers in orthodontic positioners," Am. J. Orthod. Dentofac. Orthop. 1989, 95:388–400.

Wells, "Application of the positioner appliance in orthodontic treatment," Am. J. Orthodont. 1970, 58:351–366.

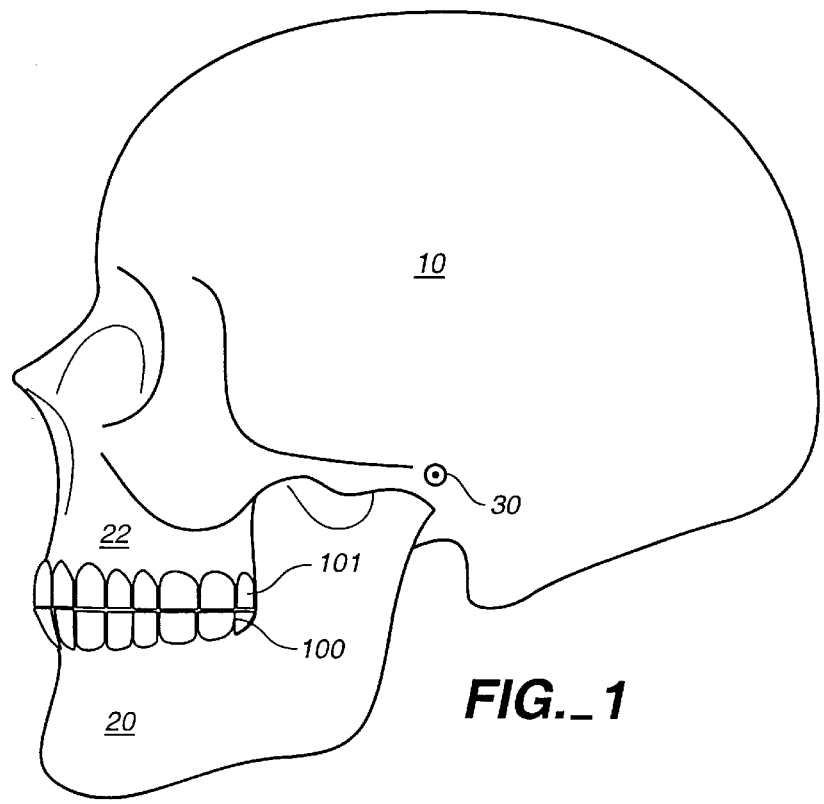
FIG._1
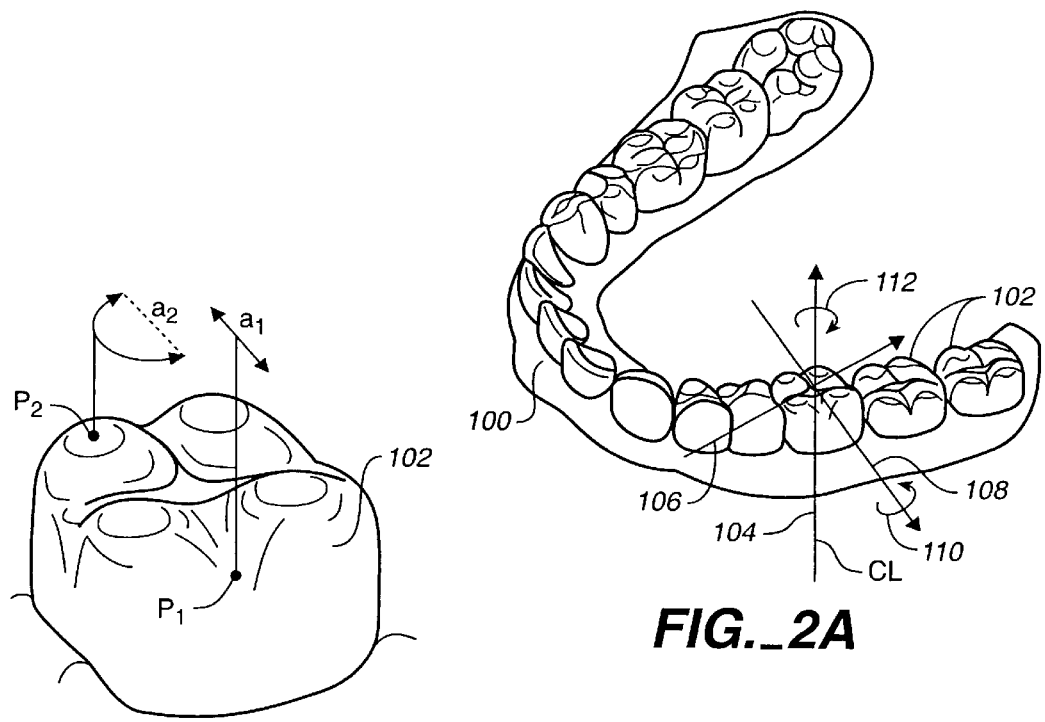
FIG._2A
FIG._2B

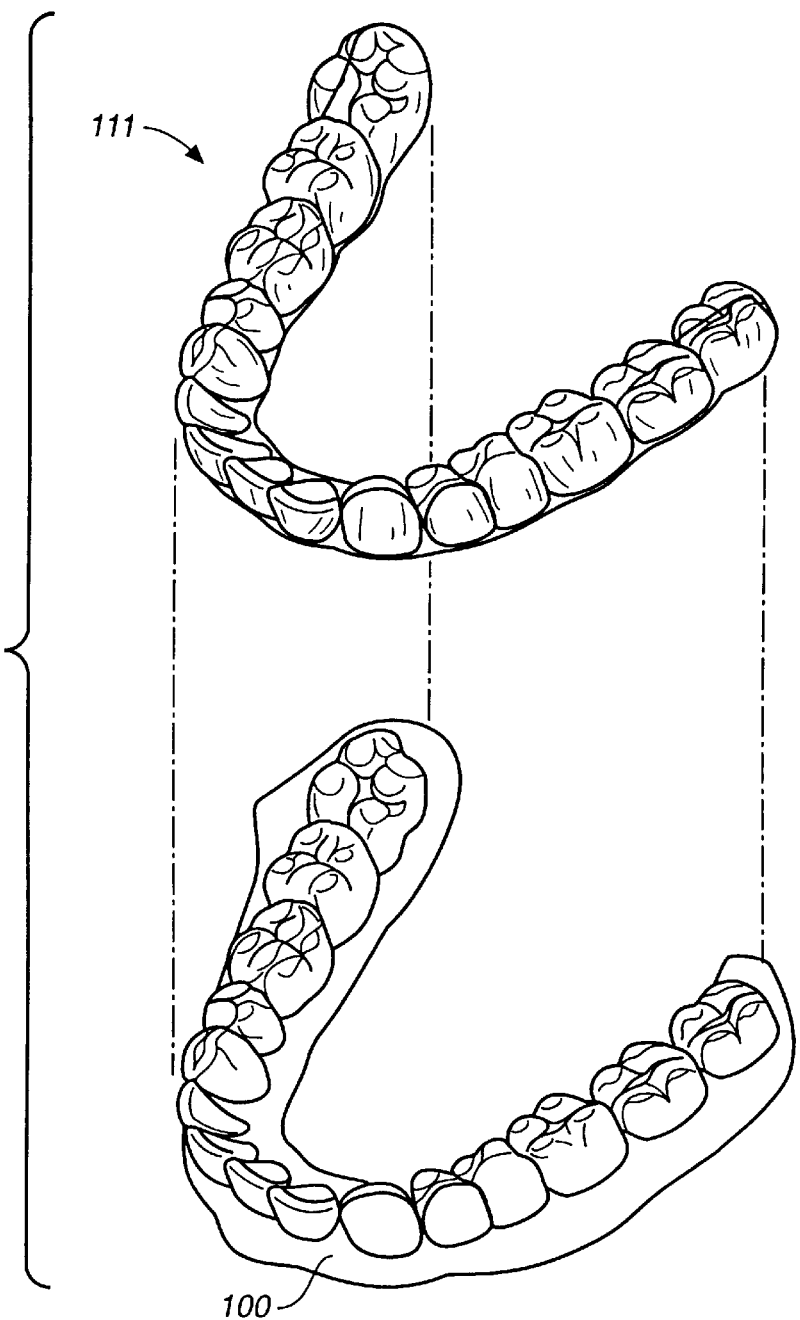
FIG._2C

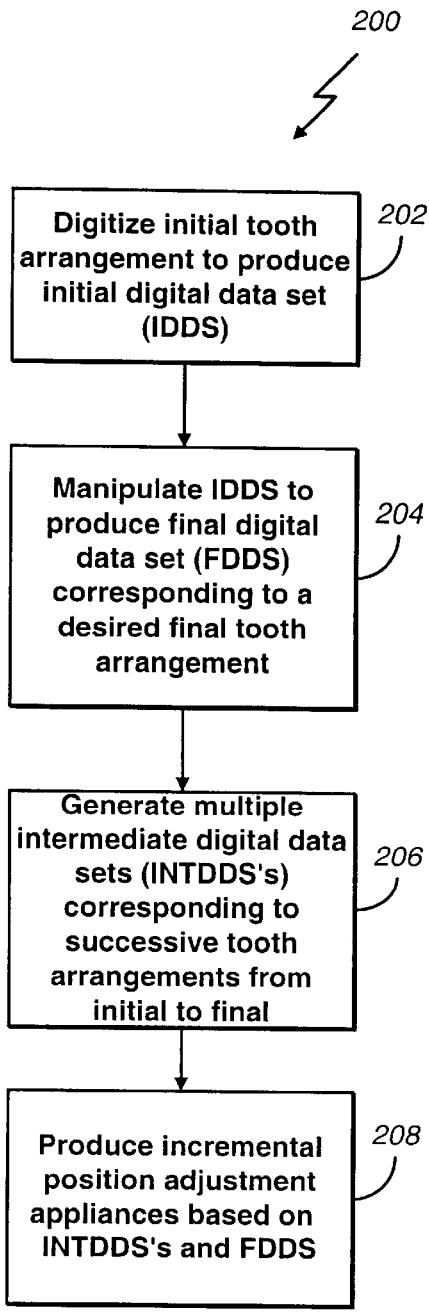
FIG._3
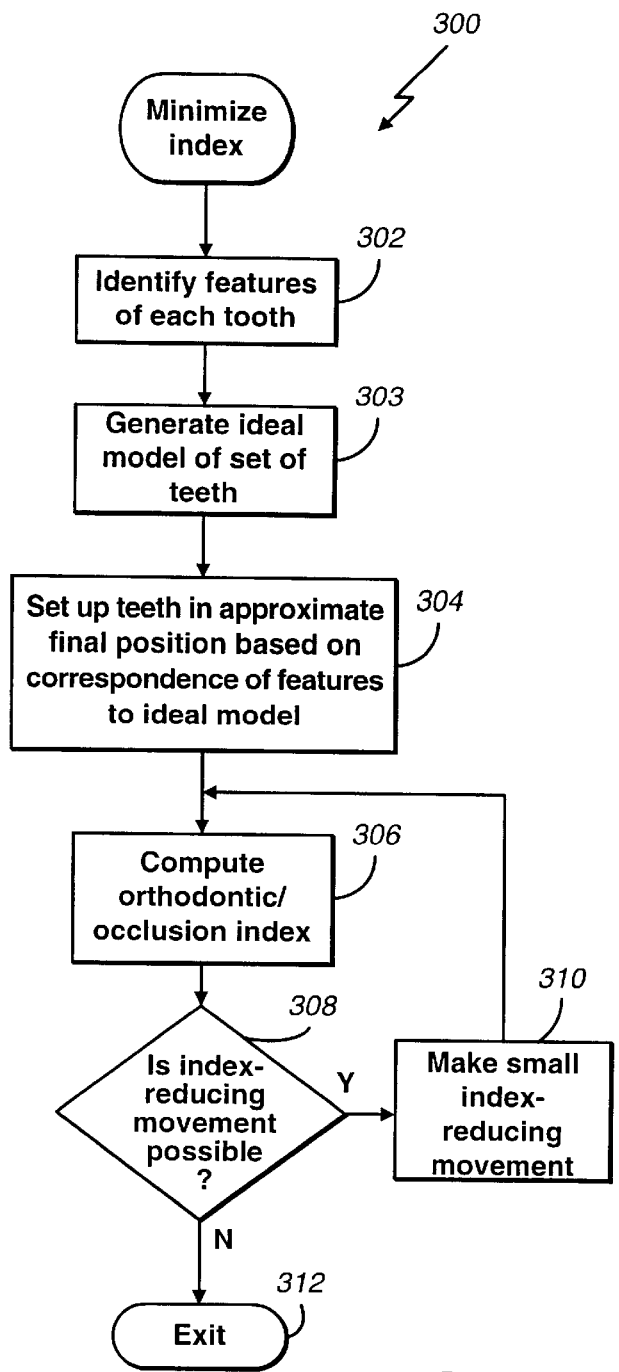
FIG._4

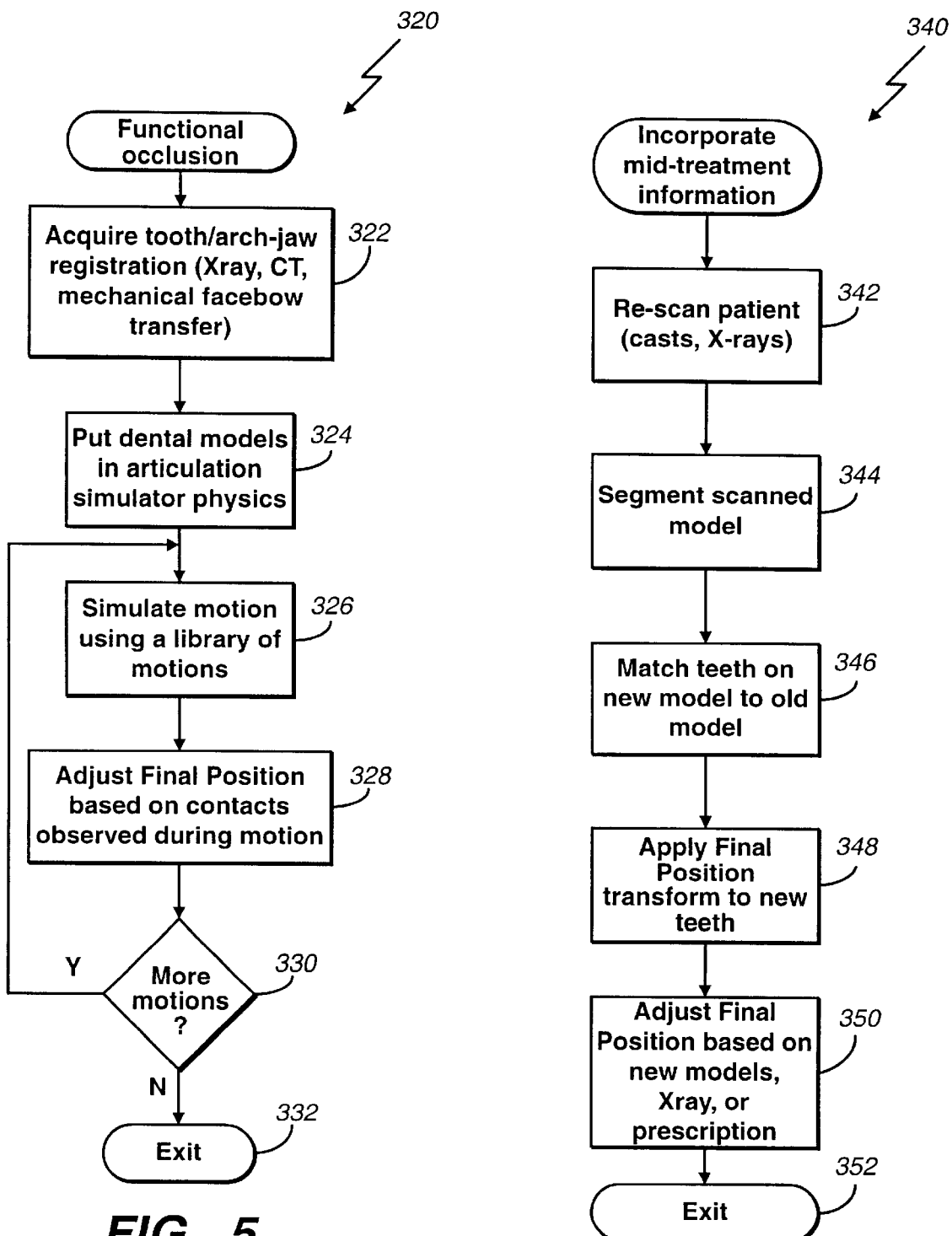

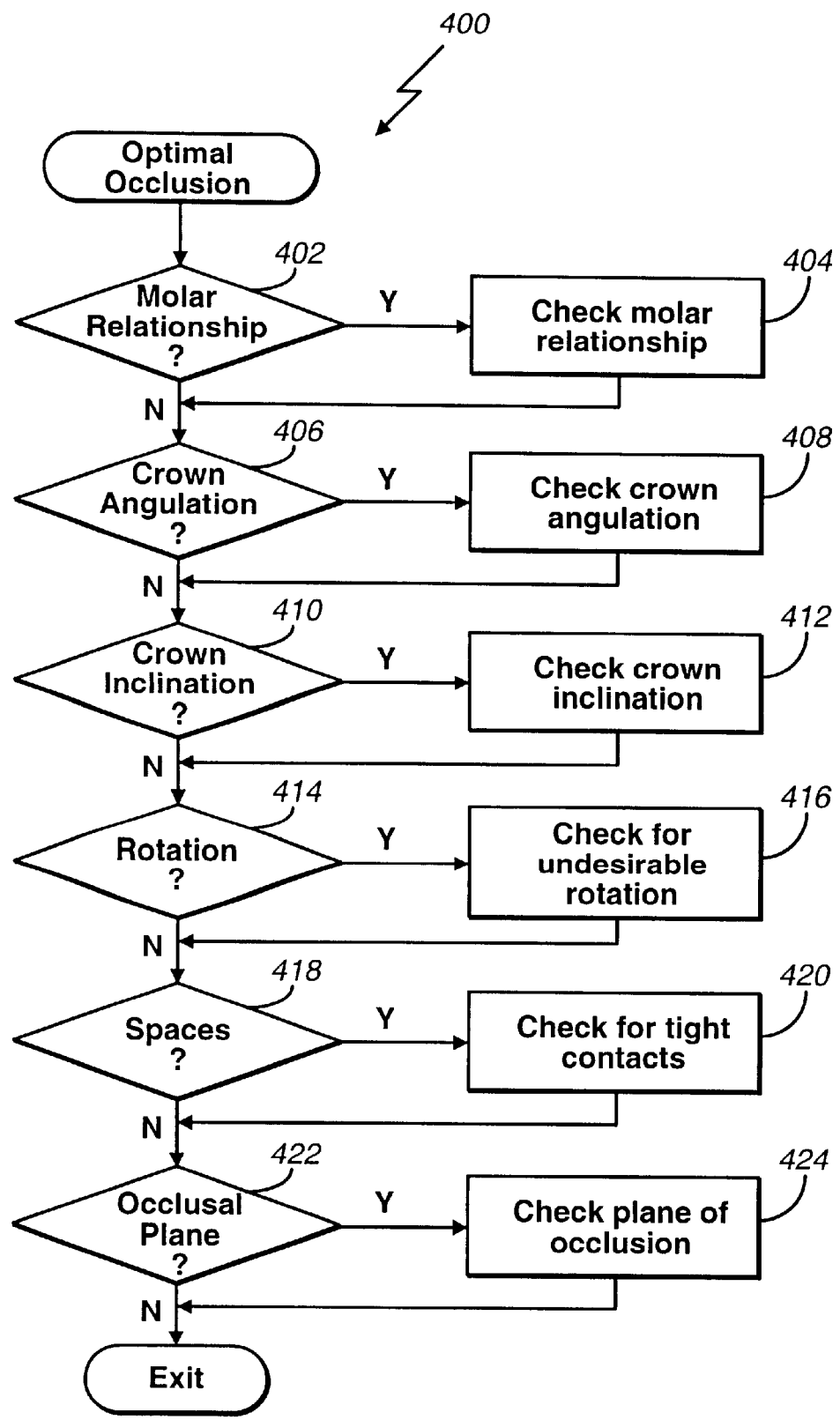
FIG._7

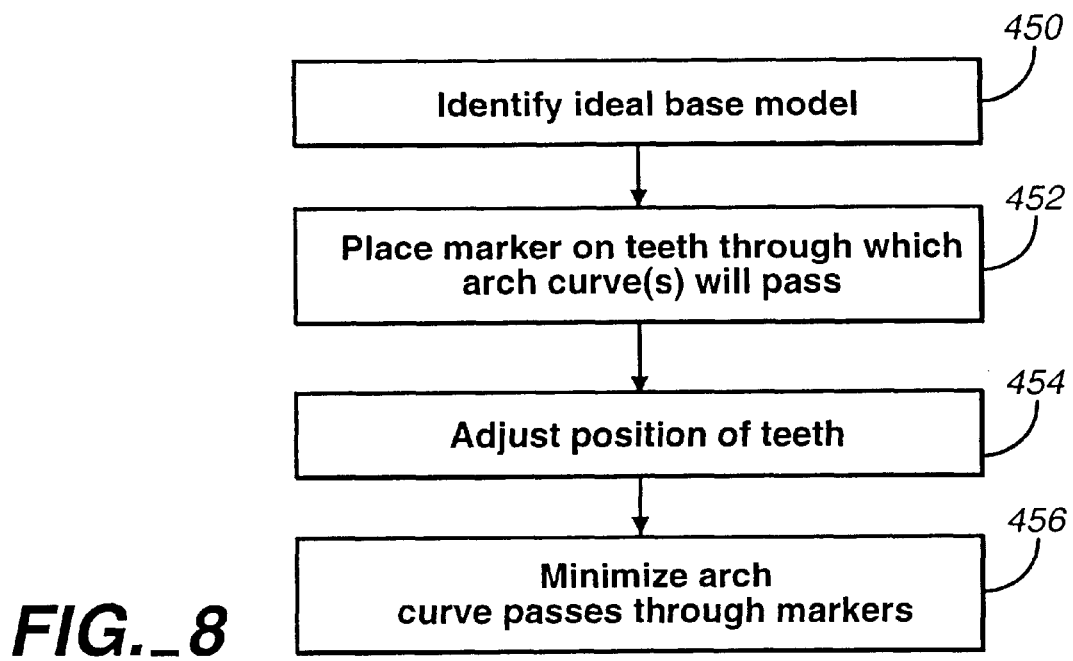
FIG._8

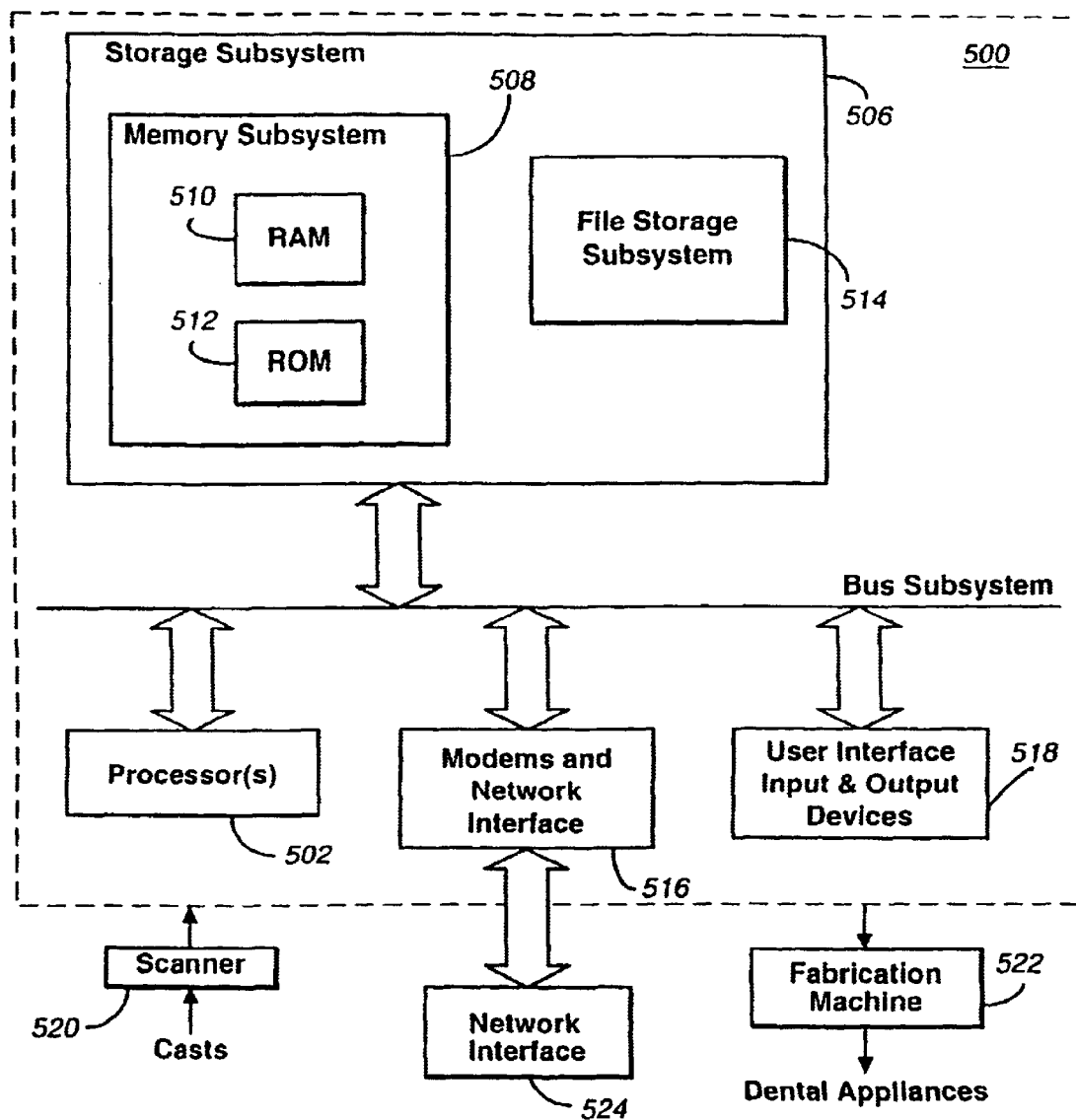
FIG._9

SYSTEM FOR DETERMINING FINAL POSITION OF TEETH

CROSS-REFERENCES TO RELATED APPLICATIONS

This application is a continuation of application Ser. No. 09/313,291, filed May 13, 1999, now U.S. Pat No. 6,406,292. The full disclosure of the above application is incorporated herein by reference.

BACKGROUND OF THE INVENTION

The present invention is related generally to the field of orthodontics, and more particularly to a system and a method for gradually repositioning teeth.

A fundamental objective in orthodontics is to realign a patient's teeth to positions where the teeth function optimally and aesthetically. Typically, appliances such as braces are applied to the teeth of the patient by a treating orthodontist. Each appliance exerts continual forces on the teeth which gradually urge the teeth toward their ideal positions. Over a period of time, the orthodontist adjusts the appliances to move the teeth toward their final destination.

The process of attaching the braces to teeth is tedious and painful. Additionally, each visit to the orthodontist is time consuming and expensive. The process is further complicated by uncertainties in determining a final arrangement for each tooth. Generally, the final tooth arrangement is determined by the treating orthodontist who writes a prescription. Traditionally, the prescription is based on the orthodontist's knowledge and expertise in selecting the intended final position of each tooth and without a precise calculation of forces being exerted on the teeth when they contact each other.

BRIEF SUMMARY OF THE INVENTION

The invention provides a method for defining a fit for a set of upper and lower teeth in a masticatory system of a patient. The fit is defined by generating a computer representation of the masticatory system of the patient and determining an occlusion from the computer representation of the masticatory system using one or more keys.

Implementations of the invention include one or more of the following. The key can be selected from a group consisting of a molar relationship, a crown angulation, a crown inclination, teeth rotations, teeth contact points, and an occlusal plane. Where the key is based on a molar relationship, a first permanent molar may be occluded with a second permanent molar. Where the first permanent molar has a disto buccal cusp with a distal surface and the second permanent molar has a mesiobuccal cusp with a mesial surface, the distal surface can occlude with the mesial surface. The mesiobuccal cusp can occlude in a groove between mesial and middle cusps of the first permanent molar. The mesial surface can approach the distal surface. Moreover, the canines and premolars of the teeth have a cusp-embrasure relationship buccally and a cusp-fossa relationship lingually.

Where the key is based on an angulation of a crown, the method can determine a distal inclination of a gingival portion of the crown. The distal inclination can be held constant for all teeth or can be constant within each tooth type. The angulation can be determined between a facial axis of the clinical crown (FACC) and a line perpendicular to an occlusal plane. The angulation can be minimized, positive or negative in value.

Where the key is based on a crown inclination, the method can determine an angle formed by a line perpendicular to an occlusal plane and a line tangent to a bracket site. The crown inclination can be negative when measured from an upper canine through an upper second premolar. The crown inclination can be progressively more negative when measured from a lower canine through a lower second molar. The crown inclination can be between a line parallel and tangent to a facial axis of the clinical crown (FACC) at its midpoint and a line perpendicular to an occlusal plane.

The key can be based on tooth rotation, or on positions where the teeth are free of undesirable rotations. The key can be based on a tooth contact point, where the contact point can be tight, where no spaces exist between contact points. The key can be based on an occlusal plane. The plane can range between flat to curves of Spee. The curve of Spee can be deep, slight, or reversed.

The method also includes optimizing a final placement of the teeth. The method can also include identifying one or more features associated with the teeth; and generating a model of the teeth based on the identified features. The features can be identified automatically or by a user. The computer representation can be an ideal model set of teeth which can be derived from a cast of the patient's teeth or from a patient with a good occlusion. The method also includes generating progress reports associated with the determined occlusion. Generated reports can be browsed over a network such as a wide area network (the Internet) or a local area network. The progress report can be viewed by a patient or a clinician. The user, which can be a clinician or a patient, manipulates the computer representation of the masticatory system.

The method also includes generating a model the teeth; and adjusting teeth position in the model by following a prescription. The method further includes generating a model of the teeth, the model having a visual appearance; and adjusting teeth position in the model until the visual appearance of the model is satisfactory. The model can be based on an abstract model of idealized teeth placement. The abstract model can be specified by one or more arch forms, or can be specified using one or more features associated with the teeth. The teeth position can be customized to the patient's teeth.

In another aspect, a system for generating one or more appliances for a patient includes a processor; a display device coupled to the processor; a data storage device coupled to the processor; a scanner coupled to the processor for providing data to model the masticatory system; means for defining a fit between a set of upper and lower teeth in a masticatory system of the patient; and a dental appliance fabrication machine coupled to the processor for generating the appliances in accordance with the fit of the teeth.

Advantages of the invention include one or more of the following. When a prescription or other final designation is provided, a computer model can be generated and manipulated to match the prescription. The prescription may be automatically interpreted in order to generate an image as well as a digital data set representing the final tooth arrangement.

BRIEF DESCRIPTION OF THE DRAWINGS

FIG. 1 is an elevational diagram showing the anatomical relationship of the jaws of a patient.

FIG. 2A illustrates in more detail the patient's lower jaw and provides a general indication of how teeth may be moved by the methods and apparatus of the present invention.

FIG. 2B illustrates a single tooth from FIG. 2A and defines how tooth movement distances are determined.

FIG. 2C illustrates the jaw of FIG. 2A together with an incremental position adjustment appliance which has been configured according to the methods and apparatus of the present invention.

FIG. 3 is a block diagram illustrating a process for producing incremental position adjustment appliances.

FIG. 4 is a flow chart illustrating a process for optimizing a final placement of the patient's teeth.

FIG. 5 is a flow chart illustrating a process for performing functional occlusion on the patient's teeth.

FIG. 6 is a flow chart illustrating an optional process for incorporating midtreatment information to the final placement of the patient's teeth.

FIG. 7 is flow chart illustrating a process for optimizing occlusion based on one or more keys.

FIG. 8 is a flow chart illustrating a second process for performing functional occlusion on the patient's teeth.

FIG. 9 is a block diagram illustrating a system for generating appliances in accordance with the present invention.

DETAILED DESCRIPTION OF THE INVENTION

FIG. 1 shows a skull 10 with an upper jaw bone 22 and a lower jaw bone 20. The lower jaw bone 20 hinges at a joint 30 to the skull 10. The joint 30 is called a temporomandibular joint (TMJ). The upper jaw bone 22 is associated with an upper jaw 101, while the lower jaw bone 20 is associated with a lower jaw 100.

A computer model of the jaws 100 and 101 is generated, and a computer simulation models interactions among the teeth on the jaws 100 and 101. The computer simulation allows the system to focus on motions involving contacts between teeth mounted on the jaws. The computer simulation allows the system to render realistic jaw movements which are physically correct when the jaws 100 and 101 contact each other. The model of the jaw places the individual teeth in a treated position. Further, the model can be used to simulate jaw movements including protrusive motions, lateral motions, and "tooth guided" motions where the path of the lower jaw 100 is guided by teeth contacts rather than by anatomical limits of the jaws 100 and 101. Motions are applied to one jaw, but may also be applied to both jaws. Based on the occlusion determination, the final position of the teeth can be ascertained.

Referring now to FIG. 2A, the lower jaw 100 includes a plurality of teeth 102, for example. At least some of these teeth may be moved from an initial tooth arrangement to a final tooth arrangement. As a frame of reference describing how a tooth may be moved, an arbitrary centerline (CL) may be drawn through the tooth 102. With reference to this centerline (CL), each tooth may be moved in orthogonal directions represented by axes 104, 106, and 108 (where 104 is the centerline). The centerline may be rotated about the axis 108 (root angulation) and the axis 104 (torque) as indicated by arrows 110 and 112, respectively. Additionally, the tooth may be rotated about the centerline, as represented by an arrow 114. Thus, all possible free-form motions of the tooth can be performed.

FIG. 2B shows how the magnitude of any tooth movement may be defined in terms of a maximum linear translation of any point P on a tooth 102. Each point $P_1$ will undergo a cumulative translation as that tooth is moved in any of the orthogonal or rotational directions defined in FIG. 2A. That is, while the point will usually follow a nonlinear path, there is a linear distance between any point in the tooth when determined at any two times during the treatment. Thus, an arbitrary point $P_1$ may in fact undergo a true side-to-side translation as indicated by arrow $d_1$, while a second arbitration point $P_2$ may travel along an arcuate path, resulting in a final translation $d_2$. Many aspects of the present invention are defined in terms of the maximum permissible movement of a point $P_1$ induced on any particular tooth. Such maximum tooth movement, in turn, is defined as the maximum linear translation of that point $P_1$ on the tooth which undergoes the maximum movement for that tooth in any treatment step.

FIG. 2C shows one adjustment appliance 111 which is worn by the patient in order to achieve an incremental repositioning of individual teeth in the jaw as described generally above. The appliance is a polymeric shell having a teeth receiving cavity. This is described in U.S. application Ser. No. 09/169,036, filed Oct. 8, 1998, which claims priority from U.S. application Ser. No. 08/947,080, filed Oct. 8, 1997, which in turn claims priority from provisional application No. 06/050,352, filed Jun. 20, 1997 (collectively the "prior applications"), the full disclosures of which are incorporated by reference.

As set forth in the prior applications, each polymeric shell may be configured so that its tooth receiving cavity has a geometry corresponding to an intermediate or final tooth arrangement intended for the appliance. The patient's teeth are repositioned from their initial tooth arrangement to a final tooth arrangement by placing a series of incremental position adjustment appliances over the patient's teeth. The adjustment appliances are generated at the beginning of the treatment, and the patient wears each appliance until the pressure of each appliance on the teeth can no longer be felt. At that point, the patient replaces the current adjustment appliance with the next adjustment appliance in the series until no more appliances remain. Conveniently, the appliances are generally not affixed to the teeth and the patient may place and replace the appliances at any time during the procedure. The final appliance or several appliances in the series may have a geometry or geometries selected to overcorrect the tooth arrangement, i.e., have a geometry which would (if fully achieved) move individual teeth beyond the tooth arrangement which has been selected as the "final." Such overcorrection may be desirable in order to offset potential relapse after the repositioning method has been terminated, i.e., to permit some movement of individual teeth back toward their precorrected positions. Overcorrection may also be beneficial to speed the rate of correction, i.e., by having an appliance with a geometry that is positioned beyond a desired intermediate or final position, the individual teeth will be shifted toward the position at a greater rate. In such cases, the use of an appliance can be terminated before the teeth reach the positions defined by the appliance.

The polymeric shell 111 can fit over all teeth present in the upper or lower 10 jaw. Often, only certain one(s) of the teeth will be repositioned while others of the teeth will provide a base or an anchor region for holding the appliance 111 in place as the appliance 111 applies a resilient repositioning force against the tooth or teeth to be repositioned. In complex cases, however, multiple teeth may be repositioned at some point during the treatment. In such cases, the teeth which are moved can also serve as a base or anchor region for holding the repositioning appliance.

The polymeric appliance 111 of FIG. 2C may be formed from a thin sheet of a suitable elastomeric polymer, such as Tru-Tain 0.03 in, thermal forming dental material, available from Tru-Tain Plastics, Rochester, Minn. Usually, no wires or other means will be provided for holding the appliance in place over the teeth. In some cases, however, it will be desirable or necessary to provide individual anchors on teeth with corresponding receptacles or apertures in the appliance 100 so that the appliance can apply an upward force on the tooth which would not be possible in the absence of such an anchor.

FIG. 3 shows a process 200 for producing the incremental position adjustment appliances for subsequent use by a patient to reposition the patient's teeth. As a first step, an initial digital data set (IDDS) representing an initial tooth arrangement is obtained (step 202). The IDDS may be obtained in a variety of ways. For example, the patient's teeth may be scanned or imaged using X-rays, three dimensional X-rays, computer-aided tomographic images or data sets, or magnetic resonance images, among others. The teeth data may be generated by a destructive scanner, as described in the incorporated-by-reference U.S. application Ser. No. 09/169,034, filed Oct. 8, 1998.

The IDDS is then manipulated using a computer having a suitable graphical user interface (GUI) and software appropriate for viewing and modifying the images. More specific aspects of this process will be described in detail below.

Individual tooth and other components may be segmented or isolated in the model to permit their individual repositioning or removal from the digital model. After segmenting or isolating the components, the user will often reposition the tooth in the model by following a prescription or other written specification provided by the treating professional. Alternatively, the user may reposition one or more teeth based on a visual appearance or based on rules and algorithms programmed into the computer. Once the user is satisfied, the final teeth arrangement is incorporated into a final digital data set (FDDS) (step 204). The FDDS is used to generate appliances that move the teeth in a specified sequence. First, the centers of each tooth model may be aligned using a number of methods. One method is a standard arch. Then, the teeth models are rotated until their roots are in the proper vertical position. Next, the teeth models are rotated around their vertical axis into the proper orientation. The teeth models are then observed from the side, and translated vertically into their proper vertical position. Finally, the two arches are placed together, and the teeth models moved slightly to ensure that the upper and lower arches properly mesh together. The meshing of the upper and lower arches together is visualized using a collision detection process to highlight the contacting points of the teeth.

Based on both the IDDS and the FDDS, a plurality of intermediate digital data sets (INTDDSs) are defined to correspond to incrementally adjusted appliances (step 206). Finally, a set of incremental position adjustment appliances are produced based on the INTDDs and the FDDS (step 208).

In step 204, final positions for the upper and lower teeth in a masticatory system of a patient are determined by generating a computer representation of the masticatory system. An occlusion of the upper and lower teeth is computed from the computer representation; and a functional occlusion is computed based on interactions in the computer representation of the masticatory system. The occlusion may be determined by generating a set of ideal models of the teeth. Each ideal model in the set of ideal models is an abstract model of idealized teeth placement which is customized to the patient's teeth, as discussed below. After applying the ideal model to the computer representation, and the position of the teeth is optimized to fit the ideal model. The ideal model may be specified by one or more arch forms, or may be specified using various features associated with the teeth.

FIG. 4 illustrates a process 300 which optimizes the final placement of the teeth based on teeth features. First, the process 300 automatically or, with human assistance, identifies various features associated with each tooth to arrive at a model of the teeth (step 302). An ideal model set of teeth is then generated either from casts of the patient's teeth or from patients with a good occlusion (step 303).

From step 302, the process 300 positions the model of the teeth in its approximate final position based on a correspondence of features to the ideal model (step 304). In that step, each tooth model is moved so that its features are aligned to the features of a corresponding tooth in the ideal model. The features may be based on cusps, fossae, ridges, distance-based metrics, or shape-based metrics. Shape-based metrics may be expressed as a function of the patient's arches, among others.

For example, cusp features associated with each tooth may be used. Cusps are pointed projections on the chewing surface of a tooth. In a detection stage, a possible cusp is viewed as an "island" on the surface of the tooth, with the candidate cusp at the highest point on the island. "Highest" is measured with respect to the coordinate system of the model, but could just as easily be measured with respect to the local coordinate system of each tooth. The set of all possible cusps is determined by looking for all local maxima on the tooth model that are within a specified distance of the top of the bounding box of the model. First, the highest point on the model is designated as the first candidate cusp. A plane is passed through this point, perpendicular to the direction along which the height of a point is measured. The plane is then lowered by a small predetermined distance along the Z axis. Next, all vertices connected to the tooth and which are above the plane and on some connected component are associated with the candidate cusp as cusps. This step is also referred to as a flood fill step. From each candidate cusp point, outward flooding is performed, marking each vertex on the model visited in this matter as part of the corresponding candidate cusp. After the flood fill step is complete, every vertex on the model is examined. Any vertex that is above the plane and has not been visited by one of the flood fills is added to the list of candidate cusps. These steps are repeated until the plane is traveled a specified distance.

After the detection stage, the cusp detection process may include a rejection stage where local geometries around each of the cusp candidates are analyzed to determine if they possess non-cusp-like features. Cusp candidates that exhibit non-cusp-like features are removed from the list of cusp candidates. Various criteria may be used to identify non-cusp-like features. According to one test, the local curvature of the surface around the cusp candidate is used to determine whether the candidate possesses non-cusp-like features. Alternatively, a measure of smoothness is computed based on the average normal in an area around the candidate cusp. If the average normal deviates from the normal at the cusp by more than a specified amount, the candidate cusp is rejected.

Next, the process 300 computes an orthodontic/occlusion index (step 306). One index which may be used is the PAR (Peer Assessment Rating) index. In addition to PAR, other metrics such as shape-based metrics or distance-based metrics may be used.

The PAR index identifies how far a tooth is from a good occlusion. A score is assigned to various occlusal traits which make up a malocclusion. The individual scores are summed to obtain an overall total, representing the degree a case deviates from normal alignment and occlusion. Normal occlusion and alignment is defined as all anatomical contact points being adjacent, with a good intercuspal mesh between upper and lower buccal teeth, and with nonexcessive overjet and overbite.

In PAR, a score of zero would indicate good alignment, and higher scores would indicate increased levels of irregularity. The overall score is recorded on pre- and posttreatment dental casts. The difference between these scores represents the degree of improvement as a result of orthodontic intervention and active treatment. The eleven components of the PAR Index are: upper right segment; upper anterior segment; upper left segment; lower right segment; lower anterior segment; lower left segment; right buccal occlusion; overjet; overbite; centerline; and left buccal occlusion. In addition to the PAR index, other indices may be based on distances of the features on the tooth from their ideal positions or ideal shapes.

From step 306, the process 300 determines whether additional index-reducing movements are possible (step 308). Here, all possible movements are attempted, including small movements along each major axis as well as small movements with minor rotations. An index value is computed after each small movement and the movement with the best result is selected. In this context, the best result is the result that minimizes one or more metrics such as PAR-based metrics, shape-based metrics or distance-based metrics. The optimization may use a number of techniques, including simulated annealing technique, hill climbing technique, best-first technique, Powell method, and heuristics technique, among others. Simulated annealing techniques may be used where the index is temporarily increased so that another path in the search space with a lower minimum may be found. However, by starting with the teeth in an almost ideal position, any decrease in the index should converge to the best result.

In step 308, if the index can be optimized by moving the tooth, incremental index-reducing movement inputs are added (step 310) and the process loops back to step 306 to continue computing the orthodontic/occlusion index. Alternatively, in the event that the index cannot be optimized any more, the process 300 exits (step 312).

Turning now to FIG. 5, a process 320 for performing functional occlusion is shown. Functional occlusion is a process for determining how well the teeth fit together when the jaws move. The process 320 first acquires tooth/arch jaw registration. This may be done using conventional techniques such as X-ray, a computer tomography, or a mechanical device such as a face bow transfer.

After acquiring the registration information, the process 320 places digital dental models of the teeth in a digital articulation simulator (step 324). The articulation simulator allows a subset of jaw movements such as bite-movements to be simulated, as described below.

From step 324, the process 320 simulates jaw motions (step 326). A simplified set of movement physics (kinematics) is applied to the dental models. The process 320 performs a simulation using a simplified set of interacting forces on the jaws 100 and 101 in relation to one another. The simplified physical simulation allows the system to focus on motions involving much contact between the jaws. The physical simulation allows the system to render realistic physically correct jaw movements when the jaws 100 and 101 come into contact with each other.

A range of simulated motion may be supplied using a library of motions. One typical motion supplied by the library is a protrusive motion where the lower jaw 101 is moved forward and backward to bring the front teeth on both jaws into contact with each other. Another motion is a lateral motion found in food chewing. The lateral motion involves moving the jaws 100 and 101 side to side. Other motions that may be supplied in the library include motions that are "tooth guided" where the path of the lower jaw 100 is guided by the teeth in contact with each other.

Next, the process 320 adjusts the final position based on contacts observed during the simulation of motions in step 326 (step 328). The result of the simulation is analyzed, the position of each tooth can be adjusted if contacts associated with that tooth are deemed excessive.

Finally, based on the contact data generated, the process determines whether additional motion simulations need to be done. The motion simulation may be rerun until the contacts associated with each tooth are acceptable to the treating orthodontist. The tooth model manipulation process can be done subjectively, i.e., the user may simply reposition teeth in an aesthetically and/or therapeutically desired manner based on observations of the final position or based on the simulation of contacts. Alternatively, rules and algorithms may be used to assist the user in repositioning the teeth based on the contacts. If the simulation needs to be repeated, the process loops back to step 326 (step 330). Alternatively, the process exits (step 332).

FIG. 6 shows an optional process of 340 of incorporating midtreatment information to the final positioning process. First, a digital model incorporating dental information associated with the patient is generated from a scan of the patient's teeth (step 342). The scan may be performed using casts, X-rays or any of the conventional scanning methods.

Next, the digital model is segmented into one model for each tooth (step 344). Each tooth is then matched against a model associated with a prior scan developed at the beginning of the treatment plan (step 346). The matching process is based on matching corresponding points between the current scan and the prior scan of the teeth. In most cases, the teeth segmented from the current scan retain the shapes determined at the beginning of the treatment plan, and the matching process is easy because the models should be similar to each other.

A final position transform is then applied to the new teeth model (step 348). The final position and specification from the prior model is copied to the current model of the patient, and the final position is adjusted based on the new models, the new X-ray information or a new prescription (step 350). Step 350 basically involves rerunning the minimization process 300 (FIG. 4) described previously with the new information, which may be a slight change in the model, a change in the X-ray scan, or a change the prescription. Finally, the process 340 exits (step 352)

FIG. 7 is a flowchart of a process 400 for determining optimal occlusion in the teeth model. The process 400 optimizes the occlusion based on six characteristics (Six Keys) that were found to be consistently present in a collection of 120 casts of naturally optimal occlusion. The keys include a molar relationship key, a crown angulation key, a crown inclination key, teeth rotation key, teeth contact point key, and an occlusal plane key. The individual keys provide a complete set of indicators of optimal occlusion, can be judged from tangible landmarks, and can be judged from a facial and occlusal surfaces of the crowns, thus reducing the need for a lingual view for articulating paper to confirm occlusial interfacing. These keys are described in Lawrence F. Andrews, "The six keys to normal occlusion," *Am. J. Orthod.* Vol. 62, No. 3 pp.296–309 (9/72) and in Chapter 3 of his book entitled Straight Wire—The Concept and Appliance (Published by L. A. Wells), the contents of which are incorporated by reference.

The Six Keys are interdependent elements of the structural system of optimal occlusion and are based on similarities in the patterns of angulation, inclination, shape, and relative size (facial prominence) of tooth types. As such, they serve as a base for evaluating occlusion. The Six Keys are used as treatment objectives for patients. The characteristics of the Six Keys are incorporated into the design of appliance 111 to enhance precision and consistency in treatment results.

The process 400 first checks whether optimization is to be done with respect to a molar relationship key (step 402). If so, the process 400 checks and applies an appropriate molar relationship (step 404). The molar relationship pertains to the occlusion and the interarch relationships of the teeth. Step 404 enforces the following seven requirements of the molar relationship key:

1. The mesiobuccal cusp of the permanent maxillary first molar occludes in the groove between the mesial and the middle buccal cusps of the permanent mandibular first molar.
2. The distal marginal ridge of the maxillary first molar occludes with the mesial marginal ridge of the mandibular second molar.
3. The mesiolingual cusp of the maxillary first molar occludes in the central fossa of the mandibular first molar.
4. The buccal cusps of the maxillary premolars have a cusp-embrasure relationship with the mandibular premolars.
5. The lingual cusps of the maxillary premolars have a cusp-fossa relationship with the mandibular premolars.
6. The maxillary canine has a cusp-embrasure relationship with the mandibular canine and first premolar. The tip of its cusp is slightly mesial to the embrasure.
7. The maxillary incisors overlap the mandibular incisors and the midlines of the arches match.

The cusp-groove and the marginal-ridge conditions of the molars, the cusp-embrasure relationship of the premolars and canines, and incisor overjet can be observed directly from the buccal perspective. A facial axis of the clinical crown (FACC) measurement is used to permit assessment of the lingual-cusp occlusion of the molars and premolars when these teeth are viewed from their mesiobuccal aspect, as explained below.

In step 404, Interarch relationship of the posterior teeth of two dentitions can be the same, but the interfacing of the occlusal surfaces of the two dentitions may differ because of differing crown inclinations.

Step 404 ensures that correct occlusal interfacing through correct interarch relationship, angulation, and crow inclination. Interarch relationship and angulation are best judged from the buccal perspective; crown inclination for posterior teeth is best judged from the dentition's mesiobuccal perspective. Judging posterior occlusion first from the buccal (for angulation and interarch relationship) then from the mesiobuccal (for inclination) provides a perspective that can be systematically described and quantified. Such information, along with other nonocclusal guidelines, are used in step 404 to identify occlusal deviations.

Step 404 includes occluding a first permanent molar with a second permanent molar. In such an occlusion, the first permanent molar has a distobuccal cusp with a distal surface, the second permanent molar has a mesiobuccal cusp with a mesial surface and the distal surface occludes with the mesial surface. The mesiobuccal cusp can occlude in a groove between mesial and middle cusps of the first permanent molar. The mesial surface can closely approach the distal surface. Moreover, where the teeth have canines and premolars, the canines and premolars have a cusp-embrasure relationship buccally and a cusp-fossa relationship lingually.

From step 402 to 404, the process 400 checks whether the occlusion needs to be optimized with respect to a crown angulation key (step 406). If so, the occlusion is optimized with respect to the crown angulation key (step 408). Essentially, step 408 ensures that all crowns should have a positive angulation, and all crowns of each tooth type should be similar in the amount of angulation. Further, the contact-area position for each tooth type should be similar. Step 408 determines a distal inclination of a gingival portion of the crown. The distal inclination may be constant within each tooth type. The angulation may be determined between the FACC and a line perpendicular to an occlusal plane. Step 408 may minimize the angulation, which may be positive or negative.

From step 406 or step 408, the process 400 checks whether the occlusion is to be optimized with respect to a crown inclination key (step 410). If so, the crown inclination optimization is performed (step 412). As they do in angulation, consistent patterns also prevail in crown inclination, the following three characteristics for individual teeth are analyzed in step 412.

1. Most maxillary incisors have a positive inclination; mandibular incisors have a slightly negative inclination. In most of the optimal sample, the interincisal crown angle is less than 180°. The crowns of maxillary incisors are more positively inclined, relative to a line 90° to the occlusal plane, than the mandibular incisors are negatively inclined to the same line.
2. The inclinations of the maxillary incisor crowns are generally positive the centrals more positive than the laterals. Canines and premolars are negative and quite similar. The inclinations of the maxillary first and second molars are also similar and negative, but slightly more negative than those of the canines and premolars. The molars are more negative because they are measured from the groove instead of from the prominent facial ridge, from which the canines and premolars are measured.
3. The inclinations of the mandibular crowns are progressively more negative from the incisors through the second molars.

In step 412, the crown inclination can represent an angle formed by a line perpendicular to an occlusal plane and a line tangent to a bracket site. In this step, the crown inclination can be negative when measured from an upper canine through an upper second premolar. The crown inclination may become progressively more negative when measured from a lower canine through a lower second molar. The crown inclination may also be positioned between a line parallel and tangent to the FACC at its midpoint and a line perpendicular to an occlusal plane.

From step 410 or 412, the process 400 checks whether the occlusion is to optimized using a rotation key (step 414). If so, the process 400 checks for undesirable rotations (step 416) and corrects the model so that tooth rotations are absent.

From step 414 or step 416, the process 400 then determines whether the occlusion needs to be optimized with respect to spacing (step 418). If so, the process 400 checks for tight contacts that is, no spaces should exist between teeth (step 420). Step 418 checks that contact points abut unless a discrepancy exists in mesiodistal crown diameter.

From step 418 or step 420, the process 400 then checks whether the occlusion is to be optimized with respect to an occlusal plane key (step 422). If so, the process 400 then optimizes the teeth model by analyzing the plane of occlusion (step 424). In step 424, the depth of the curve of Spee ranges from a flat plane to a slightly concave surface. The plane can range between flat to curves of Spee. Moreover, the curve of Spee may be deep, slight, or reversed. From step 422 or step 424, the process 400 exits.

FIG. 8 is a flow chart illustrating a second process for detremining final position of the patient's teeth. The process of FIG. 8 identifies an ideal base model for the final position of the teeth that consists of an arch curve (step 450). This model can be selected from a suite of template models, derived from patients with ideal occlusion, or derived from patient under treatment (via the casts, X-rays, a prescription, or data about the patient from other sources). Next, the user of the software places and orients a marker on each tooth, through which the arch curve (or curves) is intended to pass (step 452). The curves can be designed so that they should pass through markers placed on the tooth's facial, lingual, or occlusal surface. Multiple arch curves can be used to make the specification of the final position more accurate. In step 454, the position and orientation of the teeth are adjusted so that the arch curve passes through the marker on each tooth and the teeth do not overlap. Optionally, the teeth can be made to contact each other in this step. Next, where the teeth have multiple markers, the position and orientation of the tooth is set so that the arch curves pass as closely as possible through all markers on each tooth (step 456). In another implementation, the markers can be automatically placed and oriented on each tooth. The user can optionally adjust their position and orientation.

FIG. 9 is a simplified block diagram of a data processing system 500. Data processing system 500 typically includes at least one processor 502 which communicates with a number of peripheral devices over bus subsystem 504. These peripheral devices typically include a storage subsystem 506 (memory subsystem 508 and file storage subsystem 514), a set of user interface input and output devices 518, and an interface to outside networks 516, including the public switched telephone network. This interface is shown schematically as "Modems and Network Interface" block 516, and is coupled to corresponding interface devices in other data processing systems over communication network interface 524. Data processing system 500 may include a terminal or a low-end personal computer or a high-end personal computer, workstation or mainframe.

The user interface input devices typically include a keyboard and may further include a pointing device and a scanner. The pointing device may be an indirect pointing device such as a mouse, trackball, touchpad, or graphics tablet, or a direct pointing device such as a touchscreen incorporated into the display. Other types of user interface input devices, such as voice recognition systems, may be used.

User interface output devices may include a printer and a display subsystem, which includes a display controller and a display device coupled to the controller. The display device may be a cathode ray tube (CRT), a flat-panel device such as a liquid crystal display (LCD), or a projection device. The display subsystem may also provide nonvisual display such as audio output.

Storage subsystem 506 maintains the basic programming and data constructs that provide the functionality of the present invention. The software modules discussed above are typically stored in storage subsystem 506. Storage subsystem 506 typically comprises memory subsystem 508 and file storage subsystem 514.

Memory subsystem 508 typically includes a number of memories including a main random access memory (RAM) 510 for storage of instructions and data during program execution and a read only memory (ROM) 512 in which fixed instructions are stored. In the case of Macintosh-compatible personal computers the ROM would include portions of the operating system; in the case of IBM-compatible personal computers, this would include the BIOS (basic input/output system).

File storage subsystem 514 provides persistent (nonvolatile) storage for program and data files, and typically includes at least one hard disk drive and at least one floppy disk drive (with associated removable media). There may also be other devices such as a CD-ROM drive and optical drives (all with their associated removable media). Additionally, the system may include drives of the type with removable media cartridges. The removable media cartridges may, for example be hard disk cartridges, such as those marketed by Syquest and others, and flexible disk cartridges, such as those marketed by Iomega. One or more of the drives may be located at a remote location, such as in a server on a local area network or at a site on the Internet's World Wide Web.

In this context, the term "bus subsystem" is used generically so as to include any mechanism for letting the various components and subsystems communicate with each other as intended. With the exception of the input devices and the display, the other components need not be at the same physical location. Thus, for example, portions of the file storage system could be connected over various local-area or wide-area network media, including telephone lines. Similarly, the input devices and display need not be at the same location as the processor, although it is anticipated that the present invention will most often be implemented in the context of PCS and workstations.

Bus subsystem 504 is shown schematically as a single bus, but a typical system has a number of buses such as a local bus and one or more expansion buses (e.g., ADB, SCSI, ISA, EISA, MCA, NuBus, or PCI), as well as serial and parallel ports. Network connections are usually established through a device such as a network adapter on one of these expansion buses or a modem on a serial port. The client computer may be a desktop system or a portable system.

Scanner 520 is responsible for scanning casts of the patient's teeth obtained either from the patient or from an orthodontist and providing the scanned digital data set information to data processing system 500 for further processing. In a distributed environment, scanner 520 may be located at a remote location and communicate scanned digital data set information to data processing system 500 over network interface 524.

Fabrication machine 522 fabricates dental appliances based on intermediate and final data set information received from data processing system 500. In a distributed environment, fabrication machine 522 may be located at a remote location and receive data set information from data processing system 500 over network interface 524.

Various alternatives, modifications, and equivalents may be used in lieu of the above components. Although the final position of the teeth may be determined using computer-aided techniques, a user may move the teeth into their final positions by independently manipulating one or more teeth while satisfying the constraints of the prescription.

Additionally, the techniques described here may be implemented in hardware or software, or a combination of the two. The techniques may be implemented in computer programs executing on programmable computers that each includes a processor, a storage medium readable by the processor (including volatile and nonvolatile memory and/or storage elements), and suitable input and output devices. Program code is applied to data entered using an input device to perform the functions described and to generate output information. The output information is applied to one or more output devices.

Each program can be implemented in a high level procedural or object-oriented programming language to operate in conjunction with a computer system. However, the programs can be implemented in assembly or machine language, if desired. In any case, the language may be a compiled or interpreted language.

Each such computer program can be stored on a storage medium or device (e.g., CD-ROM, hard disk or magnetic diskette) that is readable by a general or special purpose programmable computer for configuring and operating the computer when the storage medium or device is read by the computer to perform the procedures described. The system also may be implemented as a computer-readable storage medium, configured with a computer program, where the storage medium so configured causes a computer to operate in a specific and predefined manner.

Further, while the invention has been shown and described with reference to an embodiment thereof, those skilled in the art will understand that the above and other changes in form and detail may be made without departing from the spirit and scope of the following claims.

What is claimed is:

1. A method for moving teeth, said method comprising:
   determining an occlusion from a computer model of a patient's teeth; and
   generating a plurality of appliances based on the occlusion, wherein the appliances comprise polymeric shells having cavities and wherein the cavities of successive shells have different geometries shaped to receive and resiliently reposition the teeth from one arrangement to a successive arrangement.

2. The method of claim 1, wherein determining an occlusion comprises using one or more keys.

3. The method of claim 2, wherein one of the keys is based on a molar relationship.

4. The method of claim 3, further comprising occluding a first permanent molar with a second permanent molar.

5. The method of claim 4, wherein the first permanent molar has a disto buccal cusp with a distal surface and the second permanent molar has a mesiobuccal cusp with a mesial surface and wherein the distal surface occludes with the mesial surface.

6. The method of claim 5, wherein the mesiobuccal cusp occludes in a groove between mesial and middle cusps of the first permanent molar.

7. The method of claim 4, wherein the mesial surface closely approaches the distal surface.

8. The method of claim 3, wherein the teeth include canines and premolars and wherein the canines and premolars have a cusp-embrasure relationship buccally and a cusp-fossa relationship lingually.

9. The method of claim 2, wherein one of the keys is based on an angulation of a crown.

10. The method of claim 9, wherein the crown has a distal crown tip, further comprising determining a distal inclination of a gingival portion of the crown.

11. The method of claim 10, wherein the distal inclination is constant.

12. The method of claim 10, wherein the distal inclination is constant within each tooth type.

13. The method of claim 10, wherein the angulation is determined between a facial axis of the clinical crown (FACC) and a line perpendicular to an occlusal plane.

14. The method of claim 13, wherein the angulation is minimized.

15. The method of claim 9, wherein the angulation is positive.

16. The method of claim 9, wherein the angulation is negative.

17. The method of claim 2, wherein one of the keys is based on a crown inclination.

18. The method of claim 17, wherein the crown inclination represents an angle formed by a line perpendicular to an occlusal plane and the FACC.

19. The method of claim 17, wherein the crown inclination is negative when measured from an upper canine through an upper second premolar.

20. The method of claim 17, wherein the crown inclination is progressively more negative when measured from a lower canine through a lower second molar.

21. The method of claim 17, wherein the crown inclination between a line parallel and tangent to a facial axis of the clinical crown (FACC) at its midpoint and a line perpendicular to an occlusal plane.

22. The method of claim 2, wherein one of the keys is based on tooth rotation.

23. The method of claim 22, wherein the teeth are free of undesirable rotations.

24. The method of claim 2, wherein one of the keys is based on a tooth contact point.

25. The method of claim 24, wherein the contact point is tight C.

26. The method of claim 24, wherein no spaces exist between contact points.

27. The method of claim 2, wherein one of the keys is based on an occlusal plane.

28. The method of claim 27, wherein the plane ranges between flat to curves of Spee.

29. The method of claim 28, wherein the plane is flat.

30. The method of claim 28, wherein the plane follows a curve of Spee.

31. The method of claim 30, wherein the curve of Spee is deep.

32. The method of claim 30, wherein the curve of Spee is slight.

33. The method of claim 30, wherein the curve of Spee is reversed.

34. The method of claim 2, wherein one of the keys is selected from a group consisting of a molar relationship, a crown angulation, a crown inclination, teeth rotations, teeth contact points, and an occlusal plane.

35. The method of claim 2, further comprising optimizing a final placement of the teeth.

36. The method of claim 35, further comprising:
   identifying one or more features associated with the teeth; and generating a model of the teeth based on the identified features.

37. The method of claim 36, wherein at least one of the feature is identified automatically.

38. The method of claim 37, wherein at least one of the feature is identified by a user.

39. The method of claim 36, wherein the ideal model set of teeth is derived from a cast of the patient's teeth.

40. The method of claim 36, wherein the ideal model set of teeth is derived from a patient with a good occlusion.

41. The method of claim 2, wherein the computer representation is an ideal model set of teeth.

42. The method of claim 2, further comprising generating progress reports associated with the determined occlusion.

43. The method of claim 42, further comprising browsing the generated reports over a network.

44. The method of claim 43, wherein the network is a wide area network.

45. The method of claim 44, wherein the wide area network is the Internet.

46. The method of claim 43, wherein the network is a local area network.

47. The method of claim 42, wherein the progress report is viewed by a patient.

48. The method of claim 42, wherein the progress report is viewed by a clinician.

49. The method of claim 2, wherein the user manipulates the computer representation of the masticatory system.

50. The method of claim 49, wherein the user is a patient.

51. The method of claim 50, wherein the user is a clinician.

52. The method of claim 2, further comprising:

generating a model the teeth; and adjusting teeth position in the model by following a prescription.

53. The method of claims 52, wherein the model is based on an abstract model of idealized teeth placement.

54. The method of claim 53, wherein the abstract model is specified by one or more arch forms.

55. The method of claim 54, wherein the ideal model may be specified using one or more features associated with the teeth.

56. The method of claim 52, wherein the teeth position is customized to the patient's teeth.

57. The method of claim 2, further comprising:

generating a model the teeth, the model having a visual appearance; and adjusting teeth position in the model until the visual appearance of the model is satisfactory.

58. The method of claims 57, wherein the model is based on an abstract model of idealized teeth placement.

\* \* \* \* \*

INTER PARTES REEXAMINATION CERTIFICATE (0058th)

United States Patent
Chishti et al.

(10) Number: US 6,685,469 C1
(45) Certificate Issued: *Apr. 14, 2009

(54) SYSTEM FOR DETERMINING FINAL POSITION OF TEETH

(75) Inventors: Muhammad Chishti, Sunnyvale, CA (US); Andrew Beers, Redwood City, CA (US)

(73) Assignee: Align Technology, Inc., Sunnyvale, CA (US)

Reexamination Request:
No. 95/000,172, Jul. 18, 2006

Reexamination Certificate for:
Patent No.: 6,685,469
Issued: Feb. 3, 2004
Appl. No.: 10/047,078
Filed: Jan. 14, 2002

(*) Notice: This patent is subject to a terminal disclaimer.

Related U.S. Application Data

(63) Continuation of application No. 09/313,291, filed on May 13, 1999, now Pat. No. 6,406,292.

(51) Int. Cl.
*A61C 3/00* (2006.01)

(52) U.S. Cl. .......................................................... 433/24
(58) Field of Classification Search ........................ None
See application file for complete search history.

(56) References Cited

U.S. PATENT DOCUMENTS

| | | | |
|---|---|---|---|
| 5,683,243 | A | 11/1997 | Andreiko et al. |
| 5,800,174 | A | 9/1998 | Andersson |
| 5,879,158 | A | 3/1999 | Doyle et al. |
| 5,975,893 | A | 11/1999 | Chisti et al. |
| 6,152,731 | A | 11/2000 | Jordan et al. |
| 6,244,861 | B1 | 6/2001 | Andreiko et al. |
| 6,685,469 | B2 | 2/2004 | Chishti et al. |

FOREIGN PATENT DOCUMENTS

WO  WO-98/58596 A1  12/1998

OTHER PUBLICATIONS

Osamu Yoshii, "Research on a New Orthodontic Appliance: The Dynamic Positioner, III. The General Concept of the D.P. Method and Its Therapeutic Effect, Part 1. Dental and Functional Reversed Occlusion Case Reports", Nippon Dental Review, vol. 457, Nov. 1980, pp. 146–164.

Osamu Yoshii, "Research on a New Orthodontic Appliance: The Dynamic Positioner, II. The D.P. Manufacturing Procedure and Clinical Application", Nippon Dental Review, vol. 454, Aug. 1980, pp. 107–130.

Osamu Yoshii, "Research on a New Orthodontic Appliance: The Dynamic Positioner, I. The D.P. Comcept and Implementation of Transparent Silicone Resin (Orthocon)", Nippon Dental Review, vol. 452 Jun. 1980, pp. 61–74 (Translation of Japanese language document).

Osamu Yoshii, "Research on a New Orthodontic Appliance: The Dynamic Positioner, III. The General Concept of the D.P. Method and Its Therapeutic Effect, Part 2. Skeletal Reversed Occlusion Case Reports", Nippon Dental Review, vol. 458, Dec. 1980, pp. 112–129 (Translation of Japanese language document).

Charles Daniels, The Development of the Index of Complexity, Outcome and Need (ICON), Journal of Orthodontics, vol. 27, 2000, pp. 149–162.

Andrews, L.F. (May 1989). "The Six Keys to Optimal Occulusion" Chapter 3 In *Straight Wire—the Concept and Appliance*, pp. 13–24.

(Continued)

*Primary Examiner*—Joseph A. Kaufman

(57) ABSTRACT

An apparatus and method define a fit a set of upper and lower teeth in a masticatory system of a patient by generating a computer representation of the masticatory system of the patient; and determining an occlusion from the computer representation of the masticatory system using one or more keys.

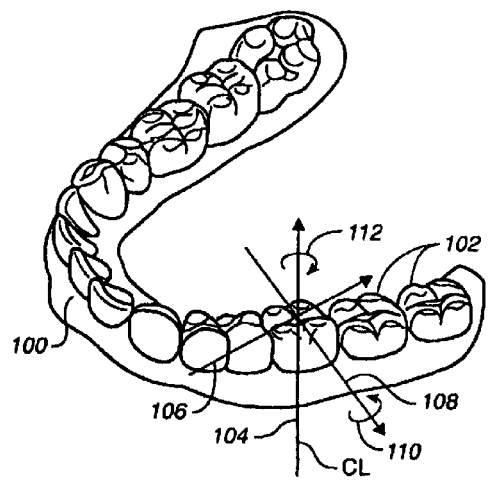

OTHER PUBLICATIONS

Andrews, L.F. (Sep. 1972). "The Six Keys to Normal Occlusion," *Am J. Orthod.* 62(3): 296–309.

Declaration of Dr. Robert G. Keim, DDS, EdD, in Support of Request of Reexamination of U.S. Appl. No. 6,685,469 Under 37 C.F.R. § 1.915.

File History of U.S. Appl. No. 09/313,291, now U.S. Patent No. 6,406,292.

File History of U.S. Appl. No. 10/047,078, now U.S. Patent No. 6,685,469.

Final Office Action in Ex Parte Reexamination of U.S. Patent No. 5,975,893, Reexamination Control No. 90/007,477, mailed Jun. 23, 2006, 17 pages.

Nahoum, H. I. (Nov. 1964), "The Vacuum Formed Dental Contour Appliance," *The New York State Dental Journal* 30(9):385–390.

Office Action in Ex Parte Reexamination of U.S. Patent No. 5,975,893, Reexamination Control No. 90/007,477, mailed Jan. 26, 2006, 55 pages.

Order Granting Request for Ex Parte Reexamination of U.S. Patent No. 5,975,893, Reexamination Control No. 90/007,477, mailed May 18, 2005, 8 pages.

INTER PARTES REEXAMINATION CERTIFICATE ISSUED UNDER 35 U.S.C. 316

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 2, 52, 53 and 55–58 are determined to be patentable as amended.

Claims 3–17, 19–24 and 26–35, dependent on an amended claim, are determined to be patentable.

New claims 59–66 are added and determined to be patentable.

Claims 18, 25, 36–51 and 54 were no reexamined.

1. A method for moving teeth, said method comprising:
   determining [an] *a functional* occlusion from a computer model of a patient's teeth, *wherein the computer model utilizes a library of simulated jaw motions*; and
   generating a plurality of appliances based on the *determined functional* occlusion, wherein the appliances comprise polymeric shells having cavities and wherein the cavities of successive shells have different geometries shaped to receive and resiliently reposition the teeth from one *computer-modeled* arrangement to a successive *computer-modeled* arrangement.

2. The method of claim 1, wherein determining [an] *the functional* occlusion comprises using one or more keys.

52. The method of claim 2, further comprising:
   generating a model *of* the teeth; and
   adjusting [teeth position] *individual tooth positions* in the model by following a prescription.

53. The method of [claims] *claim* 52, wherein the model is based on an abstract model of idealized teeth placement.

55. The method of claim 54, wherein the [ideal] *abstract* model may be specified using one or more features associated with the teeth.

56. The method of claim 52, wherein the [teeth position is] *individual tooth positions are* customized to the *positions of the* patient's teeth.

57. The method of claim 2, further comprising:
   generating a model *of* the teeth, the model having a visual appearance; and
   adjusting [teeth position] *individual tooth positions* in the model until the visual appearance of the model is satisfactory.

58. The method of [claims] *claim* 57, wherein the model is based on an abstract model of idealized teeth placement.

*59. A method for moving teeth, said method comprising:
   determining an occlusion index from a computer model of patient's teeth; and
   generating a plurality of appliances based on the occlusion index, wherein the appliances comprise polymeric shells having cavities and wherein the cavities of successive shells have different geometries shaped to receive and resiliently reposition the teeth from an initial arrangement to at least one successive intermediate arrangement to a final arrangement, wherein the at least one successive intermediate arrangement optimizes the occlusion index.*

*60. The method of claim 59, wherein the occlusion index is a peer assessment rating index.*

*61. The method of claim 59, wherein the occlusion index is a shape-based metric.*

*62. The method of claim 59, wherein the occlusion index is a distance-based metric.*

*63. A method for moving teeth, said method comprising:
   determining an occlusion index from a computer model of a patient's teeth; and
   generating a plurality of appliances based on the occlusion index, wherein the appliances comprise polymeric shells having cavities and wherein the cavities of successive shells have different geometries shaped to receive and resiliently reposition the teeth from an initial arrangement to at least one successive intermediate arrangement to a final arrangement, wherein the final arrangement optimizes the occlusion index.*

*64. The method of claim 63, wherein the occlusion index is a peer assessment rating index.*

*65. The method of claim 63, wherein the occlusion index is a shape-based metric.*

*66. The method of claim 63, wherein the occlusion index is a distance-based metric.*

\* \* \* \* \*